(12) United States Patent
Nuutinmaeki (10) Patent No.: US 8,071,939 B2
(45) Date of Patent: Dec. 6, 2011

(54) METHOD OF AND EQUIPMENT FOR MEASURING IONIC MOBILITY

(75) Inventor: Pasi Nuutinmaeki, Kalmari (FI)

(73) Assignee: Environics Oy, Mikkeli (FI)

( * ) Notice: Subject to any disclaimer, the term of this patent is extended or adjusted under 35 U.S.C. 154(b) by 563 days.

(21) Appl. No.: 12/085,687

(22) PCT Filed: Nov. 29, 2006

(86) PCT No.: PCT/FI2006/000395
§ 371 (c)(1), (2), (4) Date: Nov. 13, 2008

(87) PCT Pub. No.: WO2007/063167
PCT Pub. Date: Jun. 7, 2007

(65) Prior Publication Data
US 2009/0166526 A1 Jul. 2, 2009

(30) Foreign Application Priority Data
Nov. 30, 2005 (FI) .................................. 20051223

(51) Int. Cl.
*B01D 59/44* (2006.01)
*H01J 49/00* (2006.01)
*H01J 49/40* (2006.01)

(52) U.S. Cl. .................. 250/287; 250/281; 250/282
(58) Field of Classification Search ........... 250/281–300
See application file for complete search history.

(56) References Cited

U.S. PATENT DOCUMENTS

| | | | |
|---|---|---|---|
| 4,777,363 A | 10/1988 | Eiceman et al. | |
| 5,952,652 A * | 9/1999 | Taylor et al. | 250/286 |
| 6,180,942 B1 * | 1/2001 | Tracy et al. | 250/299 |
| 6,509,562 B1 * | 1/2003 | Yang et al. | 250/287 |
| 6,756,587 B1 * | 6/2004 | Bateman et al. | 250/287 |
| 6,787,763 B2 * | 9/2004 | De La Mora et al. | 250/287 |
| 7,217,920 B2 * | 5/2007 | Miller et al. | 250/287 |
| 7,388,195 B2 * | 6/2008 | Zapata et al. | 250/288 |
| 2003/0047681 A1 | 3/2003 | Guevremont et al. | |
| 2003/0047861 A1 | 3/2003 | Minamishin et al. | |
| 2004/0227070 A1 * | 11/2004 | Bateman et al. | 250/287 |
| 2005/0029445 A1 * | 2/2005 | Lee et al. | 250/288 |
| 2005/0098723 A1 * | 5/2005 | Farnsworth | 250/291 |
| 2005/0145789 A1 * | 7/2005 | Miller et al. | 250/290 |
| 2005/0151072 A1 * | 7/2005 | Guevremont et al. | 250/282 |

(Continued)

FOREIGN PATENT DOCUMENTS
FI 75055 C 4/1988
(Continued)

OTHER PUBLICATIONS

Carnaham et al., "Field Ion Spectrometry—A New Analytical Technology for Gas Analysis," Proceedings of the Annual ISA Analysis Division Symposium, No. 29, pp. 65-94, (1996), XP000863733.

Guevremont, "High-field asymmetric waveform ion mobility spectrometry: A new tool for mass spectrometry," Journal of Chromatogrophy, vol. 1058, No. 1-2, pp. 3-19, (2004), XP004638461.

*Primary Examiner* — Robert Kim
*Assistant Examiner* — Brooke Purinton
(74) *Attorney, Agent, or Firm* — Birch, Stewart, Kolasch & Birch, LLP (57) ABSTRACT

The invention relates to a method of and a device for measuring ion mobility, wherein ions in a medium are carried by means of an electric field and their mobility is measured. The measurement is facilitated by keeping the medium in a shear flow of the Couette type.

12 Claims, 4 Drawing Sheets

U.S. PATENT DOCUMENTS

| | | | |
|---|---|---|---|
| 2005/0178962 A1 | 8/2005 | Guevremont et al. | |
| 2005/0258363 A1* | 11/2005 | Syms | 250/292 |
| 2005/0263699 A1* | 12/2005 | Miller et al. | 250/292 |
| 2008/0067350 A1* | 3/2008 | Li | 250/287 |

FOREIGN PATENT DOCUMENTS

| | | |
|---|---|---|
| WO | WO 89/09934 A1 | 10/1989 |
| WO | WO 03/081224 A1 | 10/2003 |
| WO | WO 2006/056049 A1 | 6/2006 |

* cited by examiner

METHOD OF AND EQUIPMENT FOR MEASURING IONIC MOBILITY

BACKGROUND OF THE INVENTION

1. Field of the Invention

The invention relates to a method of measuring ionic mobility, wherein the ions in a medium are carried by means of an electric field and their mobility is measured. The invention also relates to a device for measuring the ionic mobility, comprising an electric field for carrying ions in the medium and an ion meter for measuring the ionic mobility.

The measuring device of ionic mobility herein refers to a device that is used for measuring the ionic mobility in the medium and the mobility distribution in the electric field. Generally, the medium that is measured by these devices, in practice, a gas, is ionized before the actual measurement, for example, by using a radioactive source, a corona discharge or ultraviolet light.

2. Description of the Related Art

One typical method of implementation of the device comprises a drift tube, which examines the time taken by the ions in the gas when to move a given distance under the effect of a given electric field. As ions that have different mobilities take different times travelling the distance, a mobility spectrum is obtained by means of this method. U.S. Pat. No. 4,777,363 and WO 89 09934, among others, describe the basic technique of the drift tubes. In addition, there are numerous patents that present various improvements to this technique. Typically, the technique uses a closed cycle, wherein only part of the gas that is examined is allowed to influence the actual measurement.

Another way to examine the ion mobility in gas is to use a solution of the aspiration condenser type, wherein the ions are deflected by an electric field that is perpendicular to the flow direction of the gas. Their mobility in the electric field determines, how far the ions fly before colliding either with walls or collector electrodes placed on the walls. The ions that collide with the collector electrodes generate a measurable flow, from which the ion mobility distribution of the measured gas can be deduced at a given accuracy. Typically, the ionized gas that is examined by this technique is allowed to travel as such through the measuring device. Patent FI75055, among others, describes this technique. Patent WO 03 081224 describes slightly different ways of implementing this type of cell structure; among others, a more precise way of measuring the mobility distribution by means of a reference electrode and an alternating field voltage. Applications US 2003/0047681 A1 and US 2005/0178962 A1 disclose the axial flow of a sample medium between two parallel cylindrical surfaces of an FAIMS analyzer. A challenge posed by these techniques is to equalize the gas flow travelling through the cell, among others. Furthermore, because of the open structure of the cell, any variations in the ambient temperature and, thus, also the temperature of the gas that is measured have a direct effect on the measured signal. In some cases, the laminarity of the flow and the service life of the pumps that are used for pumping the gas also pose a problem. The typical noise level of the pumps is also quite high.

SUMMARY OF THE INVENTION

The object of the invention is to correct the above-mentioned problems related to the measurement of ion mobility of the aspiration condenser type. This is mainly achieved so that, when carrying the ions in the medium by means of the electric field and measuring their mobility, the medium is kept in a shear flow, which is formed between two essentially parallels surfaces when they are moved in their own directions with respect to one another. The surfaces are preferably moved in a parallel relation with respect to one another. This is also called the Couette flow, which is the flow of a fluid formed between two parallel surfaces, when the surfaces are moved essentially in a parallel relation to one another. The shear flow is preferably maintained laminar, in other words, each particle of the medium moves essentially along a flow line of its own.

The electric field and the shear flow can be kept at an acute angle, an obtuse angle or perpendicular with respect to one another. The latter embodiment is the most useful. Typically, there are various types of ions in the medium that is carried, whereby their quantity, mobility and/or mobility distribution are measured. The method can also be implemented so that other methods of analysis are connected therewith or it is part of a more extensive analytical system.

Typically, the ion mobility is measured by means of measuring electrodes. The medium may initially contain the ions that are analyzed, or the ions can be produced by keeping the sample, which is to be analyzed, in ionizing conditions before the measurement. In that case, it is typical that the non-ionized portion of the sample is used as the medium. The sample is preferably gas and/or vapour.

Thus, the shear flow according to the invention is generated by keeping the sample and/or the medium in the shear flow between two surfaces, which move in their own planes with respect to one another and are essentially parallel. According to an embodiment of the invention, the surfaces typically consist of the opposite flat surfaces of two plates or belts. According to another embodiment of the invention, the surfaces in question consist of the outer and inner surfaces of two cylinders, which rotate with respect to each other and are of different sizes and essentially concentric. This system provides, among others, what is called the Couette-Tailor flow that belongs to the Couette flows and, thus, refers to the shear flow of matter that is formed between two essentially concentric cylinders, when one or both cylinders are rotated around their axes at different velocities with respect to the other/each other. The flow is utilized in measuring the viscosity, among others.

The method makes it easier to place the measuring electrode(s) and the source of ionization on the surface of the cylinder that is kept in place. Furthermore, when needed, the sample and/or the medium that is analyzed can be kept in the Couette-Tailor flow and suck a new quantity to be analyzed only when so desired. At the same time, the sample and/or the medium can be heated to a constant temperature and more time can be used for the analysis. Typically, the method also produces a lot less noise than the air pumps used in aspiration condenser cells.

Typically, the flow in the Couette-Tailor flow remains laminar extremely well, if the outer cylinder is rotated and the inner cylinder is kept stationaly. When rotating the inner cylinder, instead, the flow easily becomes turbulent already at fairly small operating speeds and flows. The laminar Couette-Tailor flow quite accurately follows a profile, wherein the speed of the sample and/or the medium on each surface is the same as that of the said surface, and undergoes a linear change between the same. This hypothesis holds the better, the closer the diameters of the outer surface of the inner cylinder and the inner surface of the outer cylinder are to one another. Thus, it is preferable that the ratio of the diameters of the outer surface of the inner cylinder and the inner surface of the outer cylinder is within a range of 0.30 to 0.99, preferably from 0.50 to 0.95.

When using the Couette-Taylor flow of two concentric cylinders, the sample and/or medium is typically fed between the inner and the outer cylinders and brought into shear flow therein. The sample can be fed between the cylinders on a continuous basis but it is preferable to feed it first and wait, until the flow is laminar, after which the ion mobility is measured.

It is preferable to divide the space between the cylinders into regions, wherein the flowing sample is subjected to measures related to preparation and analysis. The sample can be ionized in an ionization region that is arranged in the space between the inner and the outer cylinders. Thus, the region constitutes a circular arch between the cylinders, where the sample is mainly ionized. The ionizing conditions are provided, for example, by means of an ionizer that is arranged on the outer surface of the inner cylinder.

Correspondingly, the ions of the sample can be carried and measured in the transfer region between the inner and the outer cylinders, which is located downstream of the ionization region. Typically, this is effected by generating an electric field between the outer cylinder and the ion collector plates arranged on the inner cylinder. In that case, the number of ions and the distance travelled by them are measured by the measuring electrodes connected to the collector plate(s). The measuring electrodes for the measurement are preferably placed on the outer surface of the inner cylinder sequentially in the flow direction.

According to an embodiment, the measuring electrodes of one or more collector plates that are attached to the inner cylinder are arranged so as to widen in the direction of the shear flow. Similarly, the voltage of the electric field between the outer and the inner cylinders can be changed in the direction of the shear flow to obtain an optimal voltage profile for carrying the ions. Any turbulence of the flowing sample and/ or medium disturbs the measurement. When necessary, this can be avoided by keeping the ionizer and/or the measuring electrodes at a distance from the edges of the inner cylinder and, preferably, in the middle of the cylinder surface.

A sample that has not yet been ionized can be measured by means of reference electrodes, which are arranged upstream of the ionization region. By deducting the signal of the reference electrode from the signals of the measuring electrodes, the latter can be recovered without interference. This is of special benefit when using an alternating voltage on the outer periphery, whereby the reference electrodes can be used for eliminating the flow caused by the alternating voltage on the actual measuring electrodes. After the measurement, any ions that have drifted past the transfer region can be discharged in the zone of discharge that is located downstream of the transfer region.

The invention also relates to a device for measuring the ion mobility, comprising an electric field for transmitting ions in the medium and an ion meter for measuring the ion mobility. The device is characterized in having a first surface member that has a first surface, and a second surface member that has a second, essentially parallel surface, whereby the surfaces limit the space of the medium and can be moved by means of the surface members with respect to each other in their own directions so that, during the transmission and the mobility measurement of the ions, the medium is in shear flow. It is preferable, if the surface members are arranged so as to move the surfaces with respect to each other in a parallel relation.

As already mentioned above, the flow is preferably laminar. Thus, the surface members are preferably arranged so as to keep the medium in the laminar Couette shear flow. This is effected, for example, by keeping the surfaces strictly parallel and moving them so slowly that no turbulence or waves are generated in the flowing sample or medium. The electric field that carries the ions can be directed at a sharp angle, an obtuse angle or perpendicular to the shear flow. The angle is preferably perpendicular.

The ion meter of the device according to the invention preferably consists of one or more measuring elements that measure the amount, the mobility and/or the mobility distributions of the different types of ions. The measuring elements are preferably measuring electrodes, and there are preferably several of them. The ionizer maintains the sample, which is to be analyzed, under ionizing conditions, producing ions therefrom for the mobility measurement. The ionizer can be, for example, a UV light source, a corona discharge device or a source of radiation. It is preferably a source of radiation, e.g., an Am-241 radiation source with an activity in the order of 160 µCi.

As described above, the shear flow is generated by means of surface members, the sample to be analyzed and its possible medium being situated between the opposite, essentially parallel and moving surfaces of the surface members. The sample herein refers to the substance that is to be analyzed and the medium refers to the substance that carries the substance that is analyzed. Generally, no medium is needed, whereby the non-ionized portion of the sample functions as the medium. The sample and/or medium is preferably gas, vapour or a mixture thereof.

The surface members comprise two essentially parallel surfaces, between which there is arranged a space for the medium and/or the sample. This is the best way to accomplish the preferable laminar flow. According to a preferred embodiment of the invention, the surfaces are the opposite and essentially flat surfaces of two plates or belts. However, it is preferable that the surfaces comprise the outer and the inner surfaces of two cylinders, which rotate with respect to each other and are essentially concentric but of different sizes. In that case, the sample and/or the medium are fed into the space between the outer surface of the inner cylinder and the inner surface of the outer cylinder. When the surfaces are moved with respect to each other, the sample and/or medium flows in a manner of the Couette-Taylor type. Thus, the Couette-Taylor flow is a subtype of the Couette flow, see above. The diameters of the outer surface of the inner cylinder and the inner surface of the outer cylinder are preferably within a range of 0.30 to 0.99, and more preferably from 0.50 to 0.95.

As mentioned above, the Couette-Taylor flow is generated, when the essentially parallel surfaces of the cylinders are moved with respect to each other. Typically, the flow remains very laminar, if the outer periphery is rotated and the inner periphery is kept in place. Instead, when rotating the inner periphery, the flow becomes turbulent even at very low operating speeds and flows. In the device of the invention, thus, the inner cylinder is preferably in place and the outer cylinder is rotated. The laminar Couette-Taylor flow quite accurately follows a profile, wherein the speed of the medium on each surface is the same as that of the surface in question, changing linearly between the same. This is the truer, the closer to each other the diameters of the opposite surfaces of the cylinders are, see above.

The outer cylinder is preferably rotated by a motor. The device can also include a feeding member, which feeds the sample between the inner and the outer cylinders and brings it into shear flow therein. The feeding member preferably consists of a centrifugal fan member, which is in connection with the outer cylinder and sucks or blows the sample and/or the medium into the space between the cylinders. In that case, the motor preferably rotates both the outer cylinder and the radial wheel of the feeding member. In addition, openings in connection with the outer cylinder are typically required, through which the sample and/or the medium flows in and out of the space between the cylinders.

As mentioned in connection with the description of the method, it is preferable to feed the sample/medium into the device as a portion, and wait until it has reached the (laminar) Couette-Taylor flow. In that case, an input stream switch is needed in the feeding member of the sample to feed the sample or the medium into the space between the cylinders, whereby the measurement is not started until the batch that was fed flows in a desired manner.

Typically, the flowing space of the device according to the invention is divided into regions, where the sample is prepared and analyzed. Accordingly, the ionizer is preferably arranged in an ionizing region between the inner and the outer cylinders. The ionizer is preferably attached to the outer surface of the inner cylinder. The electric field, for its part, can be arranged in a transfer region between the inner and the outer cylinders, which is situated downstream of the ionizing region.

The electric field is generally comprised of a voltage arranged between the outer cylinder and one or more ion collector plates, which are arranged on the inner cylinder. The collector plate itself can work as a measuring electrode but, preferably, there are one or more measuring electrodes arranged in connection therewith, the number of ions and the distance travelled by them being measured with this (these) electrode(s). There are preferably several measuring electrodes, e.g., from 3 to 12, and they are typically placed on the outer surface of the inner cylinder sequentially in the direction of flow. To provide an undisturbed laminar flow, the ionizer and the measuring electrodes are arranged at a distance from the edges of the inner cylinder and, preferably, in the middle of the cylinder surface. In that case, any turbulences on the edges will not disturb the measurement. If the signal disturbances, which are directed to the measuring electrodes by the sample and/or the medium, are to be eliminated, it is preferable to arrange reference electrodes in the device, which are arranged upstream of the said ionizing region. This is of special benefit when using an alternating voltage on the outer periphery, whereby the reference electrodes can be used in eliminating the current caused by the alternating voltage on the actual measuring electrodes.

When so desired, the ions that remain after the transmission and the measurement can be removed from the shear flow. Thus, according to an embodiment, the device contains a zone of discharge that is situated downstream of the transfer region, wherein the said ions are discharged by means of a voltage. It is also preferable to arrange the ionizer, the collector plate(s) and the measuring electrodes mentioned above on a circuit board (FIG. 4), which is attached to the outer surface of the inner cylinder.

BRIEF DESCRIPTION OF THE DRAWINGS

In the following, the invention is described in detail with reference to the appended drawings that present one cell structure according to the invention.

DETAILED DESCRIPTION

Figure 1:
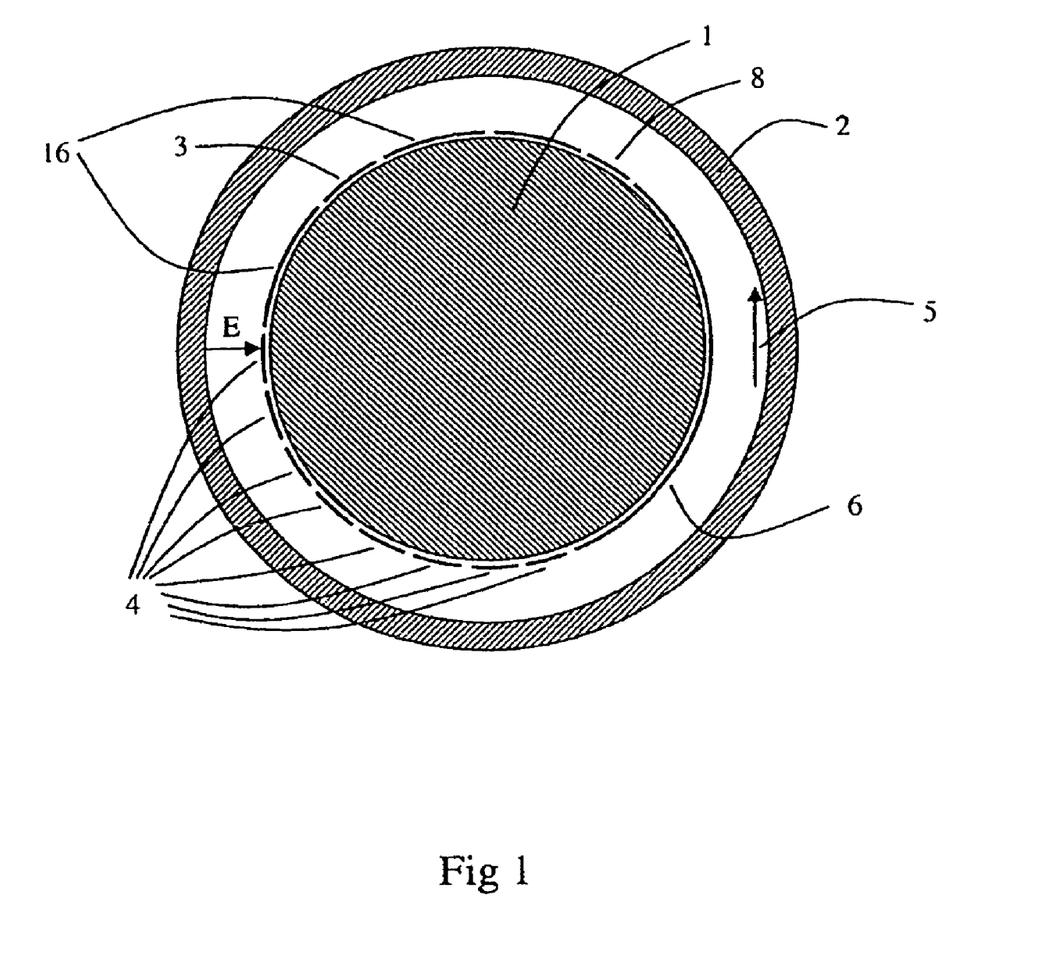
FIG. 1 shows a schematic side sectional elevation of the device according to the invention.
Figure 2:
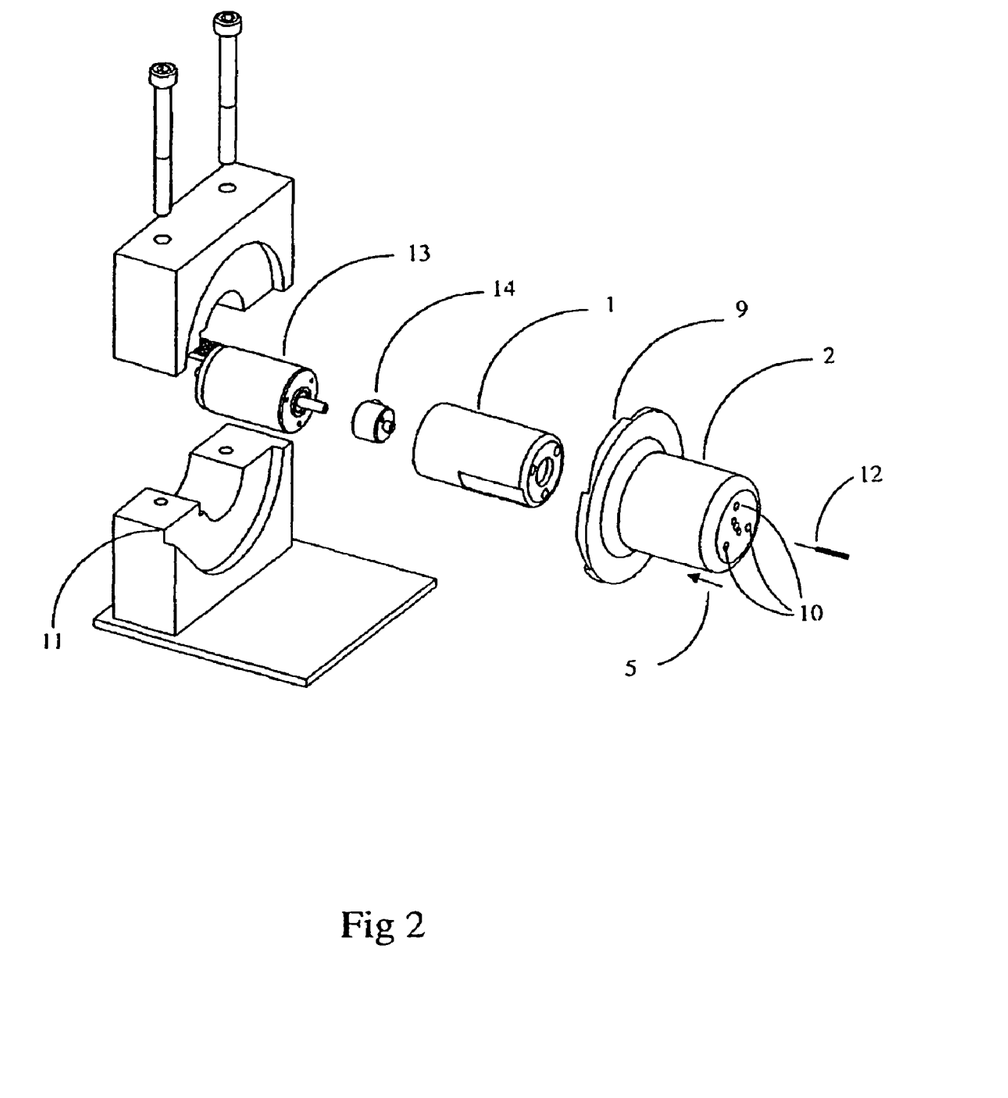
FIG. 2 shows a perspective exploded view of the same device.
Figure 3:
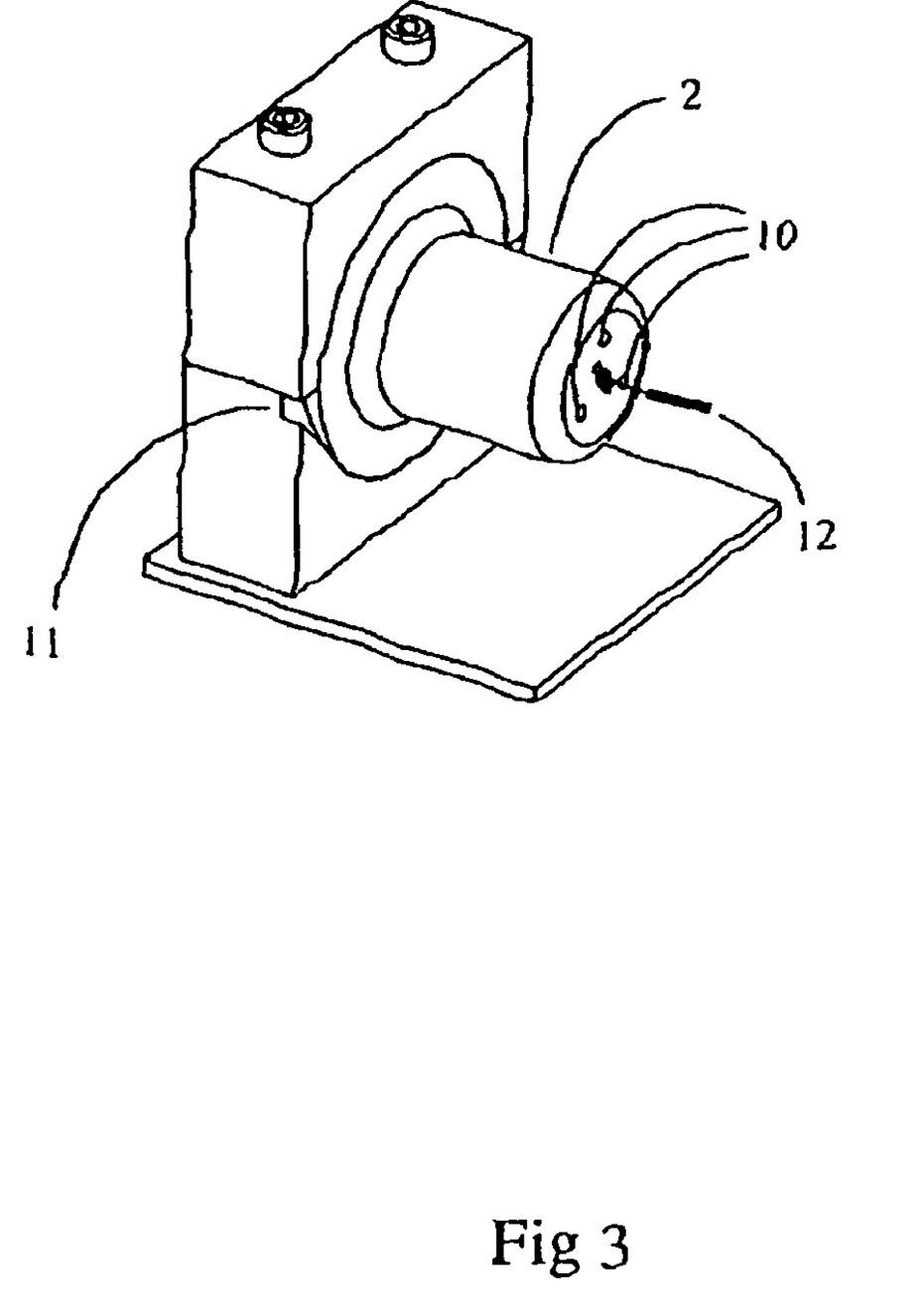
FIG. 3 shows a compact perspective view of the same device.
Figure 4:
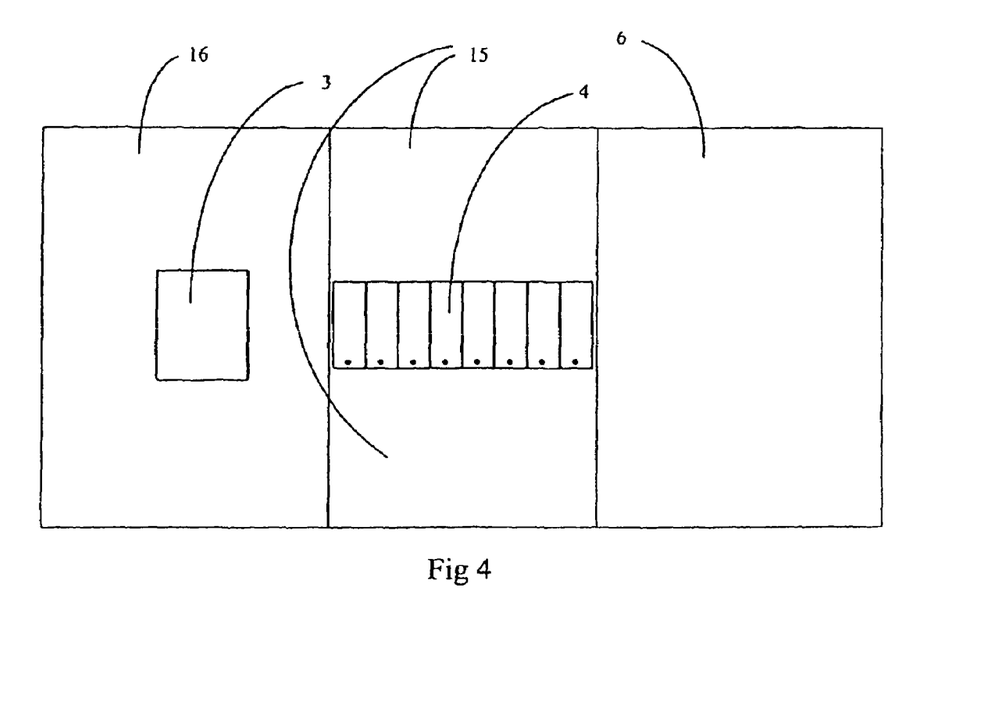
FIG. 4 shows a top view of the circuit board that is attached to the outer surface of the inner cylinder in the same device.

FIGS. 1 to 4 show a stationary inner periphery 1 having a radiation source 3 and a flexible circuit board placed on its surface, the board containing measuring electrodes 4. In this case, the outer diameter of the inner periphery without the circuit board that contains the measuring electrodes is about 25 mm. The gold-plated measuring electrodes 4 are formed onto the surface of the flexible circuit board by normal circuit board manufacturing methods. The surface of the circuit board is shown in FIG. 4, the white areas illustrating the regions of the circuit board that are metal-coated and the black areas illustrating the regions that have no metal coating; respectively. In the flow direction of gas on both sides of the measuring electrodes, there are metal-plated regions 15 that have the same voltage as the measuring electrodes. This is to make the electric field that deflects ions in this area as steady as possible. Furthermore, this arrangement reduces the disturbing currents on the measuring electrodes, which are possibly caused by surface leakage currents. For a better understanding of the scale, it should be mentioned that the width of the measuring electrodes in the figure is about 10 mm and they are spread out on a distance of about 30 mm. Conducting wires are drawn from the measuring electrodes, which are on the circuit board, by means of through holes and through drawings placed on the other side of the board, and out of the cell to the electrometer that actually measures the flow. On the board, under the radiation source 3, there is also a region 16 that typically has the same voltage as the outer periphery so as to prevent the ions from colliding with the walls before the measuring electrodes 4. The radiation source is also electrically connected to the same voltage. Correspondingly, in the direction of flow after the measuring electrodes, there is a region 6 on the circuit board, to which a voltage is connected so that the ions, which may have passed the measuring electrodes, are uncharged. The thickness of the flexible board is typically about 125 µm and that of the metal coating 35 µm. The base material of the circuit board is polyimide. This board is glued to the surface of the inner periphery 1 with the measuring electrodes pointing outward.

The outer periphery 2 is placed coaxially with the inner periphery 1 so that it rotates in the direction of arrow 5 by means of a motor 13, causing a shear flow between the inner periphery 1 and the outer periphery 2. In this case, the material of the outer periphery is stainless steel. The air gap between the outer periphery and the inner periphery 1 is about 2.3 mm and the rotational speed of the outer periphery is 1600 rotations per minute. This corresponds to a total flow rate of about 1.725 liters per minute over the measuring electrodes of a width of 10 mm. The shear flow that forms between the cylinders is implemented so that its width exceeds the outer edges of the measuring electrodes on both sides by at least twice the height of the air gap, i.e., in this case, 4.6 mm. This is because the possible turbulent areas of the edges should not interfere with the measurement. In addition, the flow on the edge zones deviates from an ideal laminar Couette-Taylor flow.

Furthermore, a transfer system of air in and out of the cell is implemented on the same axis as the outer periphery 2. This is carried out by designing the outer periphery 2 so that there is an air transfer mechanism 9 of the radial fan type on its one end, and openings 10 on the other end, from which the air to be analyzed is allowed to be absorbed inside the device. To accomplish the operation according to the invention, it should be arranged so that the axial flow in the cell, which is caused by the radial fan, will not cause a turbulence or drifting of the ions from top of the electrodes and out of the measuring region. When necessary, the most reliable way to completely prevent the axial flow is either by closing the openings 10 or an air exhaust 11. Correspondingly, the axial flow can be adjusted as desired by either changing the size of the openings 10 or the air exhaust 11 or the structure of the radial fan.

The electric field that deflects the ions is provided by bringing a voltage to the outer periphery 2 by means of a spring-loaded spike 12. This spike is in an electric contact with the middle point of the outer periphery 2. In this case, the voltage is 2.5V. The outer periphery is rotated by a motor 13, its outer casing being earthed to minimize disturbances. The rotational movement provided by the motor is transmitted to the outer periphery 2 through an intermediate part 14 that is made of electrically non-conductive material.

The gas in the flow is ionized by an Am-241 radiation source 3. The radiation source 3 is glued onto the surface of the flexible circuit board at a distance of about 1 cm from the measuring electrodes, and it is further electrically connected to the metal coating of the circuit board below. The activity of the radiation source is 160 µCi and its surface area 10*12.5 mm. For example, the ionization may possibly also be effected by means of a UV light or the ionization based on a corona discharge. Next, the ionized gas drifts along with the shear flow to the collector electrodes 4. Depending on the electric field between the outer periphery 2 and the collector plates 15 as well as the electrodes 4, the geometry of the device, the rotational speed of the outer periphery and, especially, the mobility of the ions contained in the gas in the electric field and their radial location when arriving at the collecting region, the ions move a distance characteristic of them in the electric field before colliding either with the measuring electrodes or the outer periphery. The measuring electrodes can be used in measuring the flow caused by the ions and, thus, the ion mobility distribution of the gas and the number of ions can be recognized at a given accuracy.

The figures also show a region 6, to which a voltage can be conducted in relation to the outer periphery 2, so that the ions possibly flown past the collector plates can be uncharged, depending on their polarities, by either colliding them with the outer periphery 2 or the region 6 before re-arriving at the ionizing region 3. In addition, the figure shows a reference electrode 8, which can be utilized when applying the method described in claim 1 of patent WO 03 081224. In patent WO 03 081224, the corresponding reference electrode in the figures is shown by numbers 201 and 411.

The reference electrodes 4 can be arranged in various ways for different purposes. The simplest way is to use an arrangement, wherein a desired number of electrodes are placed sequentially at equal spaces, as in the previous structural example. A second possibility is to arrange the electrodes so as to widen in the direction of flow, whereby their collecting regions are more evenly distributed to correspond to the ion mobility regions. A third possibility is to use an alternating voltage on the outer periphery and, thus, attain a larger amount of knowledge concerning the ion mobility. In the case of the alternating voltage, it may also be useful to use the reference electrode 8 in correcting the current that is generated by a capacity coupling between the outer periphery 2 and a measuring electrode(s), when the voltage of the outer periphery is changed. This method is described in detail in patent WO 03 081224. It is also possible to place, onto the outer periphery, regions of different voltages that move along with the outer periphery. This provides a corresponding effect as by changing the entire voltage of the outer periphery with respect to time.

One possible use of the invention is one, wherein new gas to be analyzed is sucked between the inner periphery 1 and the outer periphery 2 only occasionally. This enables a longer-term analysis of gas portions, and the conditions of the gas that is analyzed can be kept constant throughout the measurement. By doing this, the gas temperature, for example, can be kept constant regardless of the outer conditions and, at the same time, also decrease resources needed for the gas analysis, such as counting time, among others.

Within the invention, it is also possible to form the outer periphery so that the pumping effect required is provided by means of the same without separate pumps. In the structural example, this effect is provided by means of the radial fan.

It should be noted that within the invention, the measurement can be implemented by various ways that are quite different from each other. Among others, the measuring electrodes can be arranged in a desired way; for example, the air flow can be implemented by means of a belt travelling on a plane or by making the inner periphery the rotating part. Also the transfer of the analyzed gas in and out of the device can be arranged in various ways.

The invention claimed is:

1. A method of measuring ion mobility, wherein ions contained in a medium are carried by means of an electric field and their mobility is measured, comprising:
    keeping the medium in a shear flow that is formed between two essentially parallel surfaces by moving them in their own directions relative to one another,
    wherein the two essentially parallel surfaces consist of outer and inner surfaces of two different-sized and essentially coaxial cylinders, and
    wherein the inner cylinder is kept in place and the outer cylinder is rotated.

2. A method of measuring ion mobility, wherein ions contained in a medium are carried by means of an electric field and their mobility is measured, comprising:
    keeping the medium in a shear flow that is formed between two essentially parallel surfaces by moving them in their own directions relative to one another,
    wherein the two essentially parallel surfaces consist of outer and inner surfaces of two different-sized and essentially coaxial cylinders that rotate with respect to one another,
    wherein the ions of the sample are carried by means of an electric field in a transfer region, which is between the inner and the outer cylinders and downstream of an ionization region, and
    wherein the ion transfer is carried out by generating an electric field between the outer cylinder and one or more ion collector plates that are arranged on the inner cylinder.

3. A method of measuring ion mobility, wherein ions contained in a medium are carried by means of an electric field and their mobility is measured, comprising:
    keeping the medium in a shear flow that is formed between two essentially parallel surfaces by moving them in their own directions relative to one another,
    wherein the two essentially parallel surfaces consist of outer and inner surfaces of two different-sized and essentially coaxial cylinders that rotate with respect to one another,
    wherein the number and the drift length of the ions are measured by one or more measuring electrodes that are in connection with a collector plate, and wherein the measuring electrodes are placed on the outer surface of the inner cylinder sequentially in the direction of flow.

4. A method for measuring ion mobility wherein ions contained in a medium are carried by means of an electric field and their mobility is measured, comprising:

keeping the medium in a shear flow that is formed between two essentially parallel surfaces by moving them in their own directions relative to one another, wherein the two essentially parallel surfaces consist of outer and inner surfaces of two different-sized and essentially coaxial cylinders that rotate with respect to one another, and wherein a non-ionized sample is measured by reference electrodes, which are arranged between the inner and the outer cylinders upstream of an ionizing region.

5. A device for measuring ion mobility, comprising an electric field for carrying ions in a medium and an ion meter for measuring the ion mobility, the device comprising a first surface member that has a first surface, and a second surface member that has a second, essentially parallel surface, whereby the surfaces limit the space of the medium and can be moved by means of the surface members in their own directions and relative to each other so that, during the transfer of ions and the mobility measurement, the medium is in a shear flow, wherein the surfaces consist of outer and inner surfaces of two different-sized and essentially concentric cylinders, and wherein the inner cylinder is stationary and the outer cylinder is adapted to rotate.

6. A device according to claim 5, wherein a motor rotates the outer cylinder.

7. A device for measuring ion mobility, comprising an electric field for carrying ions in a medium and an ion meter for measuring the ion mobility, the device comprising a first surface member that has a first surface, and a second surface member that has a second, essentially parallel surface, whereby the surfaces limit the space of the medium and can be moved by means of the surface members in their own directions and relative to each other so that, during the transfer of ions and the mobility measurement, the medium is in a shear flow, wherein the surfaces consist of outer and inner surfaces of two different-sized and essentially concentric cylinders that rotate with respect to each other, wherein an ionizer is arranged in an ionizing region between the inner and the outer cylinders, and wherein the ionizer is attached to the outer surface of the inner cylinder.

8. A device for measuring ion mobility, comprising an electric field (E) for carrying ions in a medium and an ion meter for measuring the ion mobility, the device comprising a first surface member that has a first surface, and a second surface member that has a second, essentially parallel surface, whereby the surfaces limit the space of the medium and can be moved by means of the surface members in their own directions and relative to each other so that, during the transfer of ions and the mobility measurement, the medium is in a shear flow, wherein the surfaces consist of outer and inner surfaces of two different-sized and essentially concentric cylinders that rotate with respect to each other, wherein the electric field (E) is arranged in a transfer region between the inner and the outer cylinders, which is situated downstream of an ionizing region, and wherein the electric field (E) is comprised of a voltage arranged between the outer cylinder and an ion collector plate that is arranged on the inner cylinder.

9. A device according to claim 8, wherein in connection with the collector plate, one or more measuring electrodes are used for measuring the number and the transit time of the ions.

10. A device according to claim 9, wherein several measuring electrodes are placed on the outer surface of the inner cylinder sequentially in the direction of flow.

11. A device for measuring ion mobility, comprising an electric field for carrying ions in a medium and an ion meter for measuring the ion mobility, the device comprising a first surface member that has a first surface, and a second surface member that has a second, essentially parallel surface, whereby the surfaces limit the space of the medium and can be moved by means of the surface members in their own directions and relative to each other so that, during the transfer of ions and the mobility measurement, the medium is in a shear flow, wherein the surfaces consist of outer and inner surfaces of two different-sized and essentially concentric cylinders that rotate with respect to each other, and wherein reference electrodes are arranged between the inner and the outer cylinders and upstream of an ionizing region.

12. A device for measuring ion mobility, comprising an electric field for carrying ions in a medium and an ion meter for measuring the ion mobility, the device comprising a first surface member that has a first surface, and a second surface member that has a second, essentially parallel surface, whereby the surfaces limit the space of the medium and can be moved by means of the surface members in their own directions and relative to each other so that, during the transfer of ions and the mobility measurement, the medium is in a shear flow, wherein the surfaces consist of outer and inner surfaces of two different-sized and essentially concentric cylinders that rotate with respect to each other, and wherein an ionizer, a collector plate, and measuring electrodes are arranged on a circuit board, which is attached to the outer surface of the inner cylinder.

* * * * *